United States Patent
Maierhofer (10) Patent No.: US 10,532,140 B2
(45) Date of Patent: Jan. 14, 2020

(54) SYSTEM COMPRISING A PLURALITY OF MEDICAL DEVICES, PREFERABLY DIALYSIS DEVICES, AND METHODS OF OPERATING SAME

(71) Applicant: FRESENIUS MEDICAL CARE DEUTSCHLAND GMBH, Bad Homburg (DE)

(72) Inventor: Andreas Maierhofer, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 119 days.

(21) Appl. No.: 15/521,571

(22) PCT Filed: Oct. 22, 2015

(86) PCT No.: PCT/EP2015/002093
§ 371 (c)(1),
(2) Date: Apr. 24, 2017

(87) PCT Pub. No.: WO2016/062405
PCT Pub. Date: Apr. 28, 2016

(65) Prior Publication Data
US 2017/0312411 A1 Nov. 2, 2017

(30) Foreign Application Priority Data

Oct. 24, 2014 (DE) .......................... 10 2014 015 795

(51) Int. Cl.
*A61M 1/16* (2006.01)
*G06F 1/28* (2006.01)
*G16H 50/30* (2018.01)

(52) U.S. Cl.
CPC ........ *A61M 1/1613* (2014.02); *A61M 1/1601* (2014.02); *A61M 1/1605* (2014.02); *A61M 1/1656* (2013.01); *A61M 1/1664* (2014.02); *A61M 1/1666* (2014.02); *G06F 1/28* (2013.01); *A61M 2205/33* (2013.01);
(Continued)

(58) Field of Classification Search
None
See application file for complete search history.

(56) References Cited

U.S. PATENT DOCUMENTS

| | | | | |
|---|---|---|---|---|
| 2013/0191513 A1* | 7/2013 | Kamen | .................. | G06Q 10/00 709/219 |
| 2013/0211206 A1* | 8/2013 | Sands | ..................... | A61M 1/14 600/301 |
| 2014/0083917 A1* | 3/2014 | Okabe | ..................... | A61M 1/16 210/85 |

FOREIGN PATENT DOCUMENTS

| | | |
|---|---|---|
| DE | 19933223 | 1/2001 |
| EP | 0613688 | 9/1994 |

(Continued)

*Primary Examiner* — Bradley R Spies
(74) *Attorney, Agent, or Firm* — Jacobson Holman, PLLC.

(57) ABSTRACT

The invention relates to a system comprising a plurality of medical devices, preferably dialysis devices, which are connected to a common supply system, wherein the system has an evaluation unit which is connected to all devices of the system and which is configured such that values set in the different devices and/or predefined values and/or measured values, which are determined by means of at least one sensor and which relate to corresponding parameters, are compared with at least one expected value for recognizing errors of the supply system and/or of an individual device.

15 Claims, 3 Drawing Sheets

(52) U.S. Cl.
CPC ............ *A61M 2205/3317* (2013.01); *A61M 2205/3331* (2013.01); *A61M 2205/3368* (2013.01); *A61M 2205/3561* (2013.01); *G16H 50/30* (2018.01)

(56) References Cited

FOREIGN PATENT DOCUMENTS

| | | | |
|---|---|---|---|
| EP | 2716308 | 4/2014 | |
| WO | WO 2012/166377 | 12/2012 | |
| WO | WO-2012165565 A1 * | 12/2012 | ............. A61M 1/16 |

* cited by examiner

SYSTEM COMPRISING A PLURALITY OF MEDICAL DEVICES, PREFERABLY DIALYSIS DEVICES, AND METHODS OF OPERATING SAME

The treatment of dialysis patients typically takes place in dialysis centers, with a plurality of dialysis devices being connected to the same supply sources (e.g. for power, water, concentrate, etc.) and with the dialysis devices being operated under the same surrounding conditions (e.g. temperature, air humidity, brightness, etc.). Specific conditions (e.g. with respect to electrical voltage, substance concentration in the fluid, temperature, etc.) are set in the individual dialysis devices by various actuators (e.g. pumps, mixing systems, voltage regulators, etc.) in accordance with preset values at the device side or in accordance with user preset values.

Furthermore, sensors are located at suitable positions in the dialysis device which deliver measured values (e.g. electrical voltage, conductivity, temperature, etc.). An expected value can be fixed for some of these measured values on the basis of known properties of the supply sources and on the basis of preset values at the device side or on the basis of user preset values.

If a measured value deviates too far from an expected value, an error can be concluded. The deviation and consequently the error can, however, have a number of causes. For example, the cause can be found in a malfunction of an actuator or of a sensor of an individual device. Furthermore, the cause can be found in an error at the supply source which is connected to a plurality of devices.

To be able to respond properly to an error state (ensuring the optimum function of the dialysis device, recognition of potential risks for the patient), it is desirable to be able to distinguish between possible causes.

It is known in the prior art to design critical sensors in dialysis devices as redundant or to provide the possibility to compare the measured value of one sensor with that of another sensor of the same type via special comparison circuits. This requires an additional design effort. To avoid common mode errors, in principle the total measurement chain from the sensor to the evaluating electronics has to be designed as independent, which is often only possible with a high effort. Statements on the state of common supply sources of a number of devices are also hardly possible since the provided means (e.g. liquid, electrical voltage, etc.) can vary on the way to an individual device.

It is the object of the invention to provide a possibility to be able to determine causes for the deviation of a measured value from an expected value, with the disadvantages of the prior art being avoided. It is alternatively or additionally possible the underlying object of the present invention to provide a possibility to be able to determine causes for the deviation of one or more device settings and/or for the deviation of one or more user preset values from an expected value.

Against this background, the invention relates to a system comprising a plurality of medical devices which are connected to a common supply system, with provision preferably being made that the devices each have at least one sensor for determining a measured value. Provision is made in accordance with the invention that the system has an evaluation unit which is connected to all devices of the system and which is configured such that values set in the different devices and/or preset values and/or determined measured values which relate to corresponding parameters or measurement parameters are compared with at least one expected value for recognizing errors of the supply system and/or of an individual device.

In accordance with the invention, measured values and/or (device) settings, i.e. set values such as flow rates of the blood pump, of the dialyzate pump, etc., and/or (user) preset values, i.e. preset values such as a UF profile, etc., are thus compared with at least one expected value. The measured values, the set values and the preset values are also simply called "values" within the framework of the invention. The term "values" can thus comprise one or more measured values and/or set values and/or preset values.

The system preferably comprises at least three devices, with provision being able to be made that the system comprises more than five or ten devices. Provision can be made that a plurality of devices or all the devices of the system have the same type of construction or different types of construction.

The medical devices are preferably dialysis devices, wherein systems comprising a plurality of other medical devices, for example apheresis apparatus, are also covered by the invention. Devices for carrying out hemodialysis, hemofiltration or hemodiafiltration or a similar blood purification process are understood as dialysis devices.

The common supply system can, for example, be a central system for providing electrical energy and/or purified water and/or dialysis fluid concentrate and/or dialysis fluid.

The corresponding parameters or measurement parameters can be identical parameters or measurement parameters or parameters or measurement parameters in calculatory connection with one another. If the values are measured values, they can also be determined using a plurality of sensors (e.g. "blood temperature monitoring" (BTM)).

The measurement parameter can in particular be determined with the aid of an apparatus which determines the measurement parameter by means of one or more sensors by an evaluation unit, optionally after changing the treatment parameters by suitable actuators.

The sensors can, for example, be conductivity and flow sensors; the actuator can be provided, for example, for changing the dialyzate composition. A determination of the dialysis efficiency can take place using these sensors (OCM: "online clearance monitor").

The sensors can also be temperature and flow sensors and the actuator can be one which serves the changing of the dialyzate temperature. The apparatus can correspondingly be an apparatus for determining the recirculation.

The sensors for determining the corresponding measurement parameters can have the same or different types of construction or the same or different functional principles in a plurality of devices of the system.

The expected value can be an expected value specific to the device or independent of the device. An expected value specific to the device can be assumed, for example, when the expected value depends on the specific patient settings at the device. An expected value independent of the device can be assumed, for example, when the expected value is the same for all devices and does not depend on a setting at the device specific to a patient, for example. The expected value independent of the device can be based on a setting at the devices typical for the respective treatment center, e.g. a dialysis center.

In an embodiment, the evaluation unit is configured such that the expected value is a mean value of a plurality of values or measured values relating to the corresponding parameter/measurement parameter. The, for example, arithmetical mean value formation can take place via the values/measured values of all devices belonging to a specific parameter/measurement parameter. It is furthermore conceivable that the value/measured value of the device to be inspected is excluded and that the mean value formation takes place via the values/measured values of all remaining devices belonging to the specific parameter/measurement parameter.

In an embodiment, the evaluation unit is configured such that an error of the supply system is identified when measured values or other values of a plurality of devices or of all devices of the system belonging to corresponding parameters or measurement parameters deviate from the expected value or values, preferably by the same amount and/or with the same sign.

The evaluation unit therefore determines with reference to a specific rule stored in the algorithm of the evaluation unit whether a measured value deviating from the expected value or another value is limited to an individual device (there is then presumably an error in the respective device) or whether it occurs in a plurality of devices (there is then presumably an error in the supply system).

It can, for example, be identified as an error of the supply system if measured values or other values in the form of user preset values or device settings of two, of more than two or of all devices of the system belonging to corresponding parameters such as measurement parameters differ from the expected value or values. It can optionally also be taken into account in this respect whether the scheme of the deviation from the expected value is similar in each case, for instance whether the deviation has the same amount and/or the same sign.

In an embodiment, the evaluation unit is configured such that it is identified as an error of an individual device if only one or only isolated measured values or values belonging to corresponding measurement parameters or other parameters differ from the expected value or values.

The evaluation unit therefore determines with reference to a specific rule stored in the algorithm of the evaluation unit whether a measured value deviating from the expected value or another value is present for a specific device and concludes an error in the respective device on this basis.

Provision can be made that deviations from the expected value are only considered when the measured value or the other value exceeds or falls below the expected value to a specific degree, e.g. by more than 5% or 10%.

In an embodiment, the evaluation unit is configured so that a trend analysis of the comparison data is carried out with reference to which drifts in the supply system and/or of individual sensors are recognized.

The trend analysis takes place over a specific time period, for example during a treatment or a plurality of treatments. Long-term drifts in the supply system or long-term drifts of individual sensors can be recognized with reference to such an analysis. Such drifts are subsets of errors in the sense of the present invention.

In an embodiment, the evaluation unit is configured so that it is identified as a drift in the supply system when deviations of measured values or values of a plurality of devices or of all devices belonging to corresponding measurement parameters or parameters from the expected value or values increase over time.

The evaluation unit therefore determines with reference to a specific rule stored in the algorithm of the evaluation unit whether measured values or other values from two or more than two or from all devices of the system belonging to corresponding measurement parameters or other parameters differ more and more from one or more expected values over time. This suggests a drift of the supply system. It can optionally be taken into account in this respect whether the scheme of the development of the deviation is respectively similar, for instance whether an increase or decrease of the measured value/value is present in all cases.

In an embodiment, the evaluation unit is configured so that it is identified as a drift of an individual device when the deviations of only one or of only isolated measured values or other values belonging to corresponding measurement parameters/parameters from the expected value or values increase over time.

The evaluation unit therefore determines with respect to a specific rule stored in the algorithm of the evaluation unit whether an expected value differs more and more from the mean value over time for a specific device and concludes on this basis, for example, a drift of the respective sensor in the respective device.

In an embodiment, the measured value or other value in the sense of a device setting or preset user value is the conductivity of the dialysis fluid, preferably upstream of the dialyzer, and the comparison serves the recognition of errors of a central concentrate supply, of a central dialysis fluid supply, of a central pure water supply, of a dialysis fluid mixing arrangement specific to a device or of a conductivity sensor specific to a device.

In an embodiment, the measured value or other value is the conductivity, the device input pressure or the device input temperature or the RO water and the comparison serves the recognition of errors of a central RO water supply.

In an embodiment, the measured value or other value is the absolute value or the variance in the supply voltage and the comparison serves the recognition of errors in the central or device-specific power supply.

Suitable sensors for determining the measured value furthermore comprise temperature sensors, optical sensors (e.g. blood detectors) or ultrasound sensors. The sensors can be retrofitted to the devices or pre-installed thereon.

Further specific applications result from the embodiments.

In an embodiment, the system comprises a central display means and/or display means at the devices. Errors of the supply system and/or of an individual sensor can be displayed centrally and/or individually at the devices of the system. Provision can, for example, be made that an error of the supply system is displayed centrally and/or at all devices. An error of an individual device can primarily be displayed at the respective device itself and furthermore, optionally centrally, but not at the non-affected devices.

The invention further relates to a method of operating a system comprising a plurality of medical devices, preferably dialysis devices, which are connected to a common supply system, with provision preferably being made that the devices each have at least one sensor for determining a measured value. In accordance with the invention, values set in different devices of the system in operation and/or predefined values and/or determined measured values which relate to corresponding measurement parameters or to other parameters are compared with at least one expected value for recognizing errors of the supply system and/or of an individual device.

Advantageous embodiments results from the algorithm stored in the evaluation unit of the system in accordance with the invention.

Figure 1:
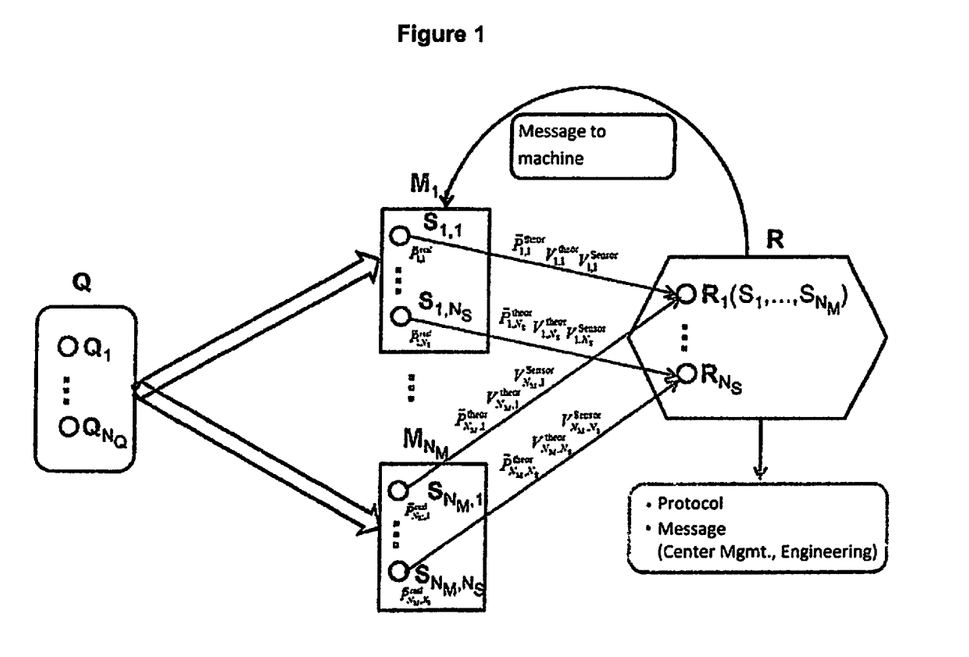
FIG. 1: a schematic representation of the structure of a system in accordance with the invention.

Further details and advantages of the invention result from the Figures and embodiments described in the following. There are shown in the Figures:

FIG. 1 shows a schematic representation of the structure of a system in accordance with the invention.

The dialysis devices $M_1$ to $M_{nM}$ are connected to the supply sources $Q_1$ to $Q_{nQ}$. The sensors $S_{j,1}$ to $S_{j,nS}$ are located in each dialysis device j. In this respect, one or more sensors can be located at one point. In real terms, the surrounding conditions $P^{real}_{j,k}=(p_1, p_2, \ldots, p_{nP})$ are present at each sensor k, where $p_1$ to $p_{nP}$ are any desired properties such as the temperature, concentration of a substance in the solution, pressures, etc.

These real properties are, however, unknown; it is rather the case that there are the assumptions about them $P^{theor}_{j,k}=(p_1, p_2, \ldots, p_{nP})$ on the basis of the settings in the dialysis device and on the basis of the assumptions on the properties of the supply sources. Based on these assumptions, an expected value $V^{theor}_{j,k}=f(P^{theor}_{j,k})$ for the measured value of the sensor is calculated in the dialysis device by means of a stored model. In real terms, this sensor, however, measures the value $V^{real}_{j,k}=f(P^{real}_{j,k})$. The values of $P^{theor}_{j,k}$, $V^{theor}_{j,k\ a}$ and $V^{real}_{j,k}$ for all sensors $S_{j,k}$ of all active dialysis devices $M_j$ are transferred to a central unit R. The deviation between the real measured value and the expected value $\Delta V_{j,k}=V^{real}_{j,k}-V^{theor}_{j,k}$ is calculated here for every sensor observed.

The frequency distribution $H\{\Delta V_{1,\lambda}, \ldots, \Delta V_{nM,\lambda}\}$ of the degree of this deviation in all dialysis devices is calculated for each suitable sensor $\lambda$. It is now examined by means of criteria stored in the central unit whether there are significant deviations for the sensor $\lambda$. If significant deviations only occur in a few machines, a conclusion is drawn that it is an isolated problem at these dialyses devices, for example a problem of an individual actuator or sensor. If the deviations are present for the greater majority of the machines, there is a high probability that it is a problem of the supply system Q. The result of this evaluation can be displayed centrally or by feedback to the respective dialysis devices.

Equally, a trend analysis of the deviation of the sensor $\lambda$ with respect to the mean value of the other sensors not showing any significant deviations can be carried out to be able to determine long-term drifts of the sensor. Conversely, deviations developing at the greater majority of the sensors can also be used for detecting drifts in the supply sources.

Figure 2:
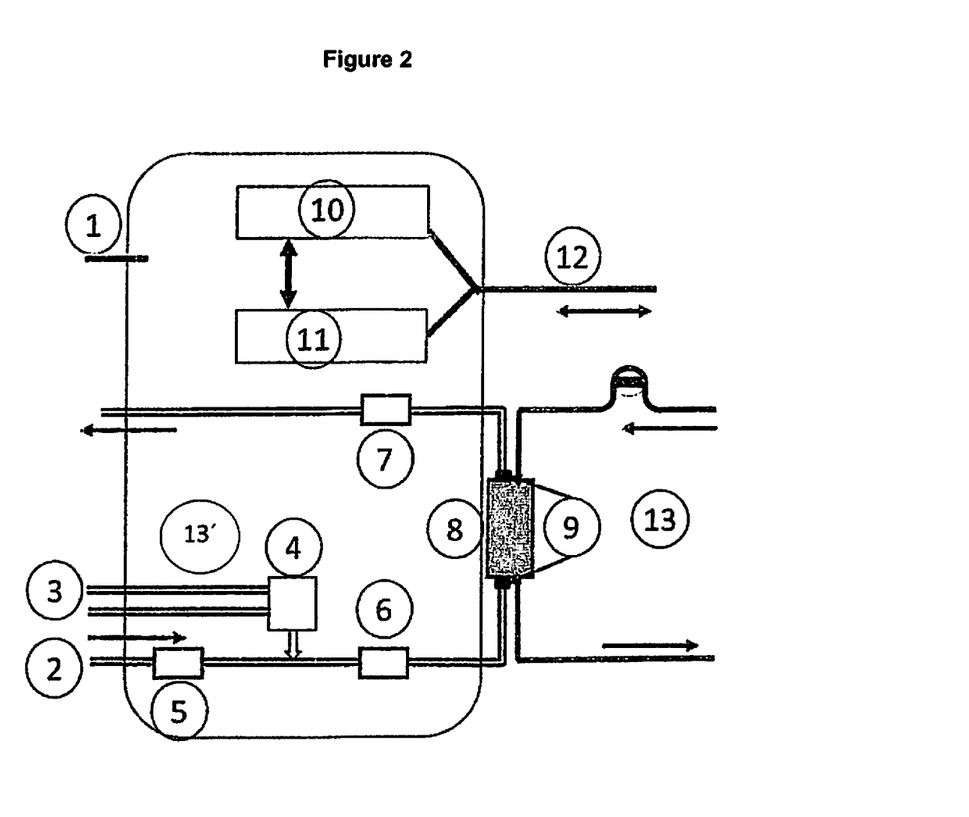
FIG. 2: a schematic representation of a dialysis device suitable for use in a system in accordance with the invention.

FIG. 2 shows a schematic representation of a dialysis device suitable for use in a system in accordance with the invention.

The dialysis device has a dialyzate circuit 13' and an extracorporeal blood circuit 13. A dialyzer 8 in which the mass transfer takes place between the dialysis fluid circulated in the dialyzate circuit and the patient's blood is coupled to the connection points 9 at the dialyzate circuit. The dialysis device is connected to a power supply 1. Furthermore, the dialysis device is connected to a supply line 2 for purified water (or RO water), with the purified water serving the production of the dialysis fluid in the mixing unit 4. One or more dialysis concentrates are selectively obtained from one or more supply lines 3. The supply lines 3 can be connected to central supply units or to reservoirs, for example. The preparation of the dialyzate from the purified water and the concentrates preferably takes place online in the mixing unit 4 which inter alia, for example, comprises pumps, lines, chambers and sensors. Conductivity sensors are marked by the reference numerals 5, 6 and 7 which measure the temperature-compensated conductivity of the RO water, of the fresh dialyzate upstream of the dialyzer and of the consumed dialyzate downstream of the dialyzer. The central supply system for a plurality of such dialysis devices therefore comprises in the present example a power supply, a system for providing purified water and a system for providing dialysis concentrate.

To be able to use concentrations of the concentrates and, further subsequently, of the dialysis fluid within the framework of the idea in accordance with the invention for recognizing errors of the supply system, the dialysis concentrate should preferably originate from the same production lot on the basis of which the expected value $V^{theor}_{j,k}$ is determined in the evaluation unit R (cf. FIG. 1) as a function of the properties of the supply source $P^{theor}_{j,k}$. The transmission of data to the evaluation unit R can, for example, take place with reference to the connection 12 according to an input of the user at the user interface 10 of the dialysis device or after an automatic recognition, e.g. via barcode readers or RFID. These measured values are transmitted to the control unit 11 of the shown dialysis device which then transmits the measured values $V^{real}_{j,k}$ to a central evaluation unit R (cf. FIG. 1) using the connection 12. Data, for example reports of an error, can also be received from the central control unit R using the connection 12.

In addition to the functions belonging to the idea of the present invention, the device's own control unit 11 also takes over known tasks such as the control of the dialysis procedure by controlling the various actuators in the dialysis device when processing user preset values from the user interface 10 and the measured sensor values from the dialysis device.

All the examples described below are based on a system in which nM dialysis devices of the type shown in FIG. 2 are connected together in a system of the type shown in FIG. 1.

EXAMPLE 1

This example deals with the distinction between the malfunction of a conductivity sensor and an erroneous electrolyte concentration in the central supply system for the concentrate of the dialysis fluid.

In a dialysis device taken by way of example from the system, the dialysis fluid is produced online, with the device obtaining the concentrate via the central supply 3 and RO water via the central supply 2. The non-consumed dialysis fluid with the real composition $P^{real}_{j,k}$ is present downstream of the mixing unit 4 and upstream of the dialyzer 8, the composition also resulting from the mixture of concentrate and RO water on the implementation of user preset values. The temperature-compensated real conductivity $V^{real}_{j,k}$ of the non-consumed dialysis fluid is measured using the conductivity sensor 6. The expected value for the conductivity $V^{theor}_{j,k}$ results from the assumed composition of the dialysis fluid $P^{theor}_{j,k}$ which results from the user preset values and the known composition of the concentrate (e.g. desired values for sodium ions and bicarbonate ions).

All nM dialysis devices transmit the values of $V^{real}_{j,k}$ and $P^{theor}_{j,k}$ and/or $V^{theor}_{j,k}$ to the evaluation unit R. Here, the deviation of the measured conductivity from the desired conductivity $\Delta V_{j,k}=V^{real}_{j,k}-V^{theor}_{j,k}$ is calculated.

Since the expected values of the conductivity are also known for different user preset values, it is not necessary that the same settings are present at all dialysis devices. In order, however, optionally to be able to determine problems of the concentrate supply, only data of machines having the same concentrate source should enter into the evaluation on a connection of different concentrate sources.

Figure 3:
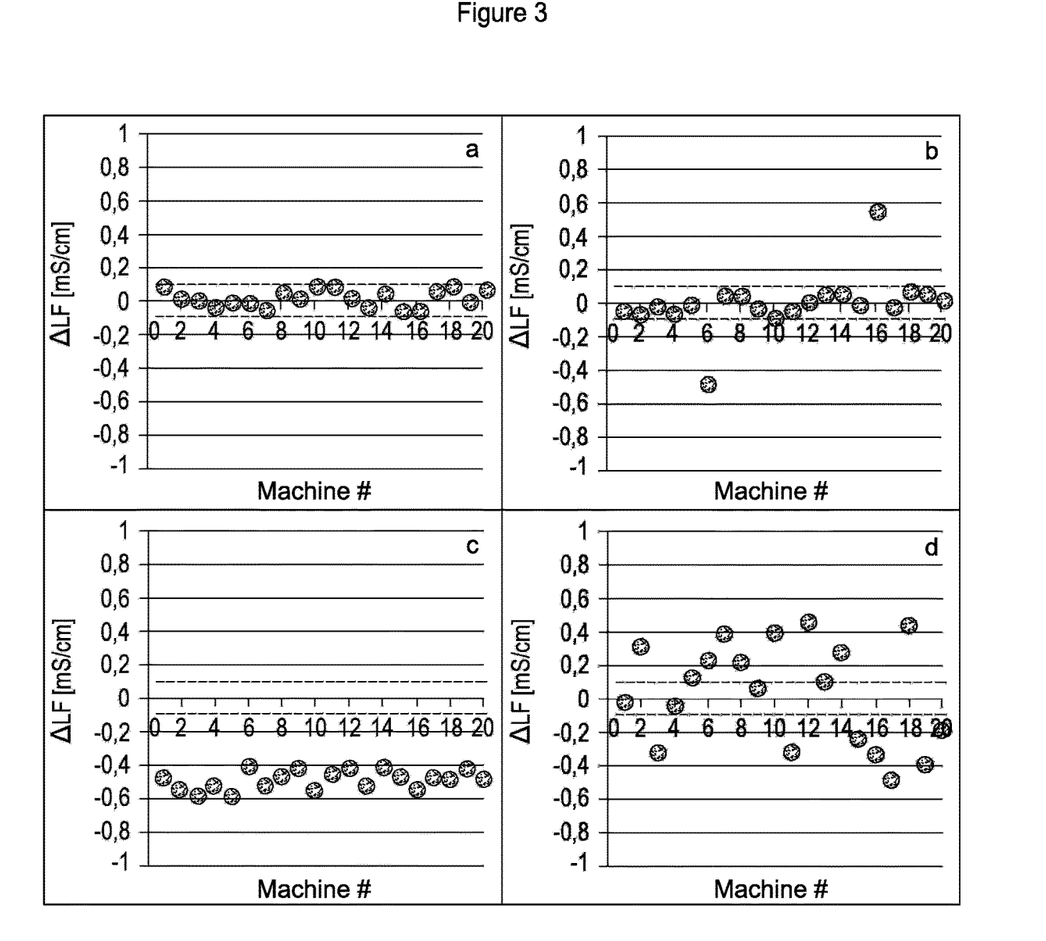
FIG. 3: graphs of deviation scenarios of the conductivity of the dialysis fluid which can be evaluated within the framework of the system in accordance with the invention.

The following scenarios are possible:

1. In all dialysis devices, $\Delta V_{j,k}$ (that is $\Delta LF_j$) is smaller than the tolerated deviation, e.g. 0.1 mS/cm. It follows from this that both the central concentrate supply and the mixing system specific to the device and the sensor specific to the device satisfy their functions properly in all machinery. This scenario is shown in the graph in accordance with FIG. 3a.
2. In a few machines, $\Delta LF_j$ is outside the tolerated deviation, whereas the tolerance is observed in all other machines. This scenario is shown in the graph in accordance with FIG. 3b, wherein $\Delta LF_j$ lies outside the tolerated deviation for the machines having the numbers 6 and 16. It follows from this that there is a problem in the mixing system or at the conductivity sensor in the machines having the numbers 6 and 16.
3. $\Delta LF_j$ is outside the tolerated deviation in all the machines, or at least in the major portion of the machines, with the degree and direction of the deviation being the same. This scenario is shown in the graph in accordance with FIG. 3c. It follows from this that a problem in the central concentrate supply is probable.
4. $\Delta LF_j$ is outside the tolerated deviation in all the machines, or at least in the major portion of the machines, with the degree and direction of the deviation, however, being completely different. An engineer call-out is necessary, but a diagnosis of the cause is not yet possible. This scenario is shown in the graph in accordance with FIG. 3d.

In addition, forecasts on the reaching of a critical parameter of the measurement error of the LF cells of a dialysis device is possible by an analysis of the long-term trend of the individual and collective deviation between the measured $\Delta LF_j$ and the expected value. Drifts in the composition of the central concentrate (e.g. caused by evaporation) or in the quality of the RO (reverse osmosis for providing the purified water) can likewise be recognized.

It is possible also to include further conductivity sensors in the monitoring by corresponding bypass circuits (e.g. bypassing the dialyzer 8). For example, the conductivity sensor 7 arranged downstream of the dialyzer can be included in the monitoring. Instead of a conductivity sensor, sensors could also be used which are specifically sensitive to individual dialyzate components, e.g. ion-selective electrodes or pH electrodes. Instead of a central concentrate supply, the same principle can be used on the use of dialysis concentrate from a reservoir, with here the lot tolerance being used as an additional factor.

EXAMPLE 2

This example deals with the distinction between the malfunction of a conductivity sensor and a defective RO water supply.

As in Example 1, in a dialysis device taken by way of example from the system, the dialysis fluid is produced online in the present case, with the device obtaining the concentrate via the central supply 3 and RO water via the central supply 2. RO water having the real composition $P^{real}_{j,k}$ (residual portion of electrolytes) is present upstream of the mixing unit 4. The temperature-compensated real conductivity $V^{real}_{j,k}$ of the RO water is measured using the conductivity sensor 5. The expected value for the conductivity $V^{theor}_{j,k}$ results from the typical purity of the RO water $P^{theor}_{j,k}$ used for dialysis treatments. It amounts to less than 0.05 µS/cm.

The principle of the evaluation takes place analogously to Example 1.

The criterion for a device problem or source problem is here formed by values of $\Delta LF_j$, wherein in turn a distinction can be made between problems of individual devices and a problem of the central RO supply. In the same manner, instead of the conductivity sensor 5, other sensors located at the same position can be used for monitoring specific properties of the RO supply, e.g. pressure sensors for monitoring the water input pressure. It can e.g. be determined by means of temperature sensors in an integrated hot cleaning whether the minimum required temperature is reached and a distinction can be made whether problems may be present in individual devices (sensor defects, cooling in hose line which is too long) or whether there is a general failure of the central cleaning apparatus. The LF monitoring can also take place in the same manner for the different concentrate feed lines.

EXAMPLE 3

This example deals with the determination of temperature fluctuations at the installation location of individual dialysis devices of the system.

The real surrounding temperature $P^{real}_{j,k}=V^{real}_{j,k}$ is measured by temperature sensors $S_{j,k}$ at the input side of a power pack fan or housing fan. The usual room temperature (optionally the mean value of the individual measured values) is used as the expected value $P^{theor}_{j,k}=V^{theor}_{j,k}$.

The principle of the evaluation takes place analogously to Example 1.

Deviations at individual devices can in this respect e.g. indicate increased heat development at the device (electronics). A more sensitive recognition of overheating is possible by the comparison with the other devices than on a comparison with a previously determined absolute limit. If the position of the devices in the clinic is included in $P^{real}_{j,k}$, a local temperature deviation in the clinic (e.g. due to incident solar radiation, malfunction of the air-conditioning or ventilation, etc.) can be recognized.

EXAMPLE 4

This example deals with the determination of errors in the central or device-specific power supply.

The supply voltage $P^{real}_{j,k}$ is measured with time resolution by a suitable voltage sensor at the voltage supply 1 of the dialysis device. The mean value of the measured voltage after a statistical evaluation or also the variance of the voltage fluctuations serves as the measured value $V^{real}_{j,k}$. A constant voltage supply having a nominal value in accordance with the specification of the utility supplier is assumed as the expected value $P^{theor}_{j,k}=V^{theor}_{j,k}$.

Deviations of the mean value or an increased variance in the supply voltage at individual devices have as their cause technical problems of the devices themselves (e.g. loose contact), of the connection (e.g. overload of a phase) or of the measurement electronics. If these problems occur in the plurality of devices, this indicates a general problem with the electrical supply, which can in particular occur in technically less developed regions such as developing countries.

EXAMPLE 5

This example deals with the determination of deviations from typical settings of a dialysis center.

Measured dialysis parameters such as conductivity, temperature, flow rates or the like serve as so-called "measured values" $P^{real}_{j,k}$, here equal to $V^{real}_{j,k}$. The corresponding center-specific typical dialysis parameters serve as the expected values $V^{theor}_{j,k}$.

As in Example 3, the exact position of the expected values is determined by the mean value over the individual measured values of the same sensors of the different dialysis devices. Alternatively, the expected values thus determined can also be stored by the processing unit. The mean value of these expected values over a plurality of treatment days can then serve for the comparison.

Deviations of the dialysis parameters from the center standard at one of the dialysis devices can arise by incorrect inputs of the dialysis parameters by the user. Deviations of the measurement parameters can be caused by malfunctions in automatic regulators, e.g. of the dialyzate flow, of the blood pump rate, of the temperature or of the dialysis composition. In these cases, the user can be prompted to check his settings and the correction function of the automatic regulators.

EXAMPLE 6

This example deals with the determination of deviations in the clearance.

All sensors required for determining the clearance serves as sensors $S_{j,option}$ in this example. For the determination of the clearance by OCM, sensors 6 and 7 serve for this purpose for the time-resolved recording of the temperature-compensated conductivity upstream and downstream of the dialyzer 8 and sensors for determining the flow of blood, dialyzate and substitute (determination of the UF rate).

The effective cleaning performance of the dialyzer for urea during the dialysis while taking account of patient effects such as recirculation, expressed in dialyzer parameters $(K_0A)_{effective}$ is assumed as the real condition $P^{real}_{j,OCM}$ at the sensors.

The assumed condition $P^{theor}_{j,OCM}$ at the sensor corresponds to the dialyzer parameter $(K_0A)_{effective}$ while assuming the recirculation typical for the dialyzer type (e.g. 10-15% cardiopulmonary recirculation).

The measured value of the sensor $V^{real}_{j,OCM}$ is the clearance and/or the dialyzer parameter $(K_0A)_{effective}$.

The measured value of the sensor $V^{theor}_{j,OCM}$ is the clearance and/or the dialyzer parameter $(K_0A)_{effective}$ while assuming the recirculation typical for the dialyzer type (e.g. 10-15% cardiopulmonary recirculation). Alternatively, on use of the center-specific dialysis parameters (cf. Example 5), the mean value of all dialyses in the system taking place under the same conditions or from the analysis of historic treatments is used as a reference.

OCM can be taken as an example for a generalized sensor in which the reaching of a physical parameter requires a complex apparatus of control unit and various sensors. The evaluation is possible as explained in Example 1:

A deviation of the clearance below the expected value in a few patients indicates problems (increased recirculation, clotting of the dialyzer, unfavorable settings of the dialysis parameters, defective connection of patient and dialyzer) in these patients. If in contrast the clearance is reduced in the greater number of patients, a general problem in the current dialysis shift in the center can be concluded from this. This problem could e.g. be a lot problem of the dialyzers used or incorrect operation by the staff (e.g. connection of the dialyzers 9 in co-current flow instead of in counter-flow by staff not familiar with the device type).

The invention claimed is:

1. A system comprising
   a) multiple dialysis devices connected to
   b) a common supply system, and
   c) an evaluation unit connected to all the dialysis devices of the system and configured such that values set in each of the dialysis devices and/or preset values and/or measured values determined by at least one sensor which relate to corresponding parameters are compared with at least one expected value for recognizing errors of the supply system and/or of an individual device, wherein the value is the absolute value or the variance of the supply voltage, and wherein the comparison serves the recognition of error in a central or device-specific power supply.

2. A system in accordance with claim 1, characterized in that the evaluation unit is configured such that the expected value is a mean value of a plurality of values relating to the corresponding parameters.

3. A system in accordance with claim 1, characterized in that the evaluation unit is configured such that an error of the supply system is identified if values of a plurality of the dialysis devices or of all the dialysis devices of the system belonging to corresponding parameters deviate from the expected value or values.

4. A system in accordance with claim 1, characterized in that the evaluation unit is configured so that an error of an individual dialysis device is identified if only one value or only isolated values belonging to corresponding parameters deviate from the expected vale or values.

5. A system in accordance with claim 1, characterized in that the evaluation unit is configured so that a trend analysis of the comparison data is carried out with reference to which drifts in the supply system and/or of individual sensors are recognized.

6. A system in accordance with claim 5, characterized in that the evaluation unit is configured so that a drift of the supply system is identified if deviations of values of a plurality of the dialysis devices or of all the dialysis devices of the system belonging to corresponding parameters increase from the expected value or values over time.

7. A system in accordance with claim 5, characterized in that the evaluation unit is configured so that a drift of an individual dialysis device is identified if the deviations of only one value or of only isolated values belonging to corresponding parameters increase from the expected value or values over time.

8. A method of operating a system in accordance with claim 1, characterized in that values set in each of the dialysis devices of the system in operation and/or predefined values and/or measured values determined by at least one sensor, which set values, redefined values, and measured values relate to corresponding parameters, are compared with at least one expected value for recognizing the errors of the supply system and/or of an individual dialysis device.

9. A method in accordance with claim 8, characterized in that the expected value is a mean value of a plurality of values relating to the corresponding parameters.

10. A method in accordance with claim 8, characterized in that an error of the supply system is identified if values of a plurality of the dialysis devices or of all the dialysis devices of the system belonging to corresponding parameters deviate from the expected value or values.

11. A method in accordance with claim 8, characterized in that an error of an individual dialysis device is identified if only value or if only isolated values belonging to corresponding parameters differ from the expected value or values.

12. A method in accordance with claim 8, characterized in that a trend analysis of the comparison data is carried out with reference to which drifts are recognized in the supply system and/or in individual sensors.

13. A system in accordance with claim 1, characterized in that the evaluation unit is configured such that an error of the supply system is identified if values of a plurality of the dialysis devices or of all the dialysis devices of the system belonging to corresponding parameters deviate from the expected value or values, by the same amount and/or by the same sign.

14. A method in accordance with claim 8, characterized in that an error of the supply system is identified if values of a plurality of the dialysis devices or of all the dialysis devices of the system belonging to corresponding parameters deviate from the expected value or values, by the same amount and/or by the same sign.

15. A method in accordance with claim 8, characterized in that a trend analysis of the comparison data is carried out with reference to which drifts are recognized in the supply system and/or in individual sensors, wherein provision is made that a drift of the supply system is identified if deviations of values of a plurality of the dialysis devices or of all the dialysis devices of the system belonging to corresponding parameters increase from the expected value or values over time, and/or wherein provision is made that a drift of an individual dialysis device is identified if the deviations of only one value or of only isolated values belonging to corresponding parameters increase from the expected value or values over time.

* * * * *